United States Patent
Khouri et al.

(10) Patent No.: US 9,522,058 B2
(45) Date of Patent: *Dec. 20, 2016

(54) METHOD AND DEVICES FOR TISSUE EXPANSION

(71) Applicant: KhouRigotti, LLC, Key Biscayne, FL (US)

(72) Inventors: Roger K. Khouri, Key Biscayne, FL (US); Gino Rigotti, S. Floriano (IT); Guido Baroni, Monsa (IT)

(73) Assignee: KhouRigotti, LLC, Key Biscayne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/743,968

(22) Filed: Jun. 18, 2015

(65) Prior Publication Data
US 2016/0000551 A1 Jan. 7, 2016

Related U.S. Application Data

(63) Continuation of application No. 14/219,576, filed on Mar. 19, 2014, now Pat. No. 9,066,795, which is a continuation of application No. 13/390,453, filed as application No. PCT/US2012/024782 on Feb. 11, 2012, now Pat. No. 8,821,573.

(60) Provisional application No. 61/453,271, filed on Mar. 16, 2011.

(30) Foreign Application Priority Data

Feb. 11, 2011 (IT) .............................. PD2011A0041

(51) Int. Cl.
| A61F 2/12 | (2006.01) |
| A61F 2/04 | (2013.01) |
| A61F 13/14 | (2006.01) |
| A61H 7/00 | (2006.01) |
| A61H 9/00 | (2006.01) |
| A61B 17/00 | (2006.01) |

(52) U.S. Cl.
CPC .................. *A61F 2/04* (2013.01); *A61B 90/02* (2016.02); *A61F 2/12* (2013.01); *A61F 13/145* (2013.01); *A61H 7/00* (2013.01); *A61B 2017/00796* (2013.01); *A61F 2230/0069* (2013.01); *A61H 9/0057* (2013.01); *A61H 2009/0064* (2013.01); *A61H 2201/165* (2013.01); *A61H 2205/082* (2013.01)

(58) Field of Classification Search
CPC .................................. A61F 2/12; A61H 7/00
(Continued)

(56) References Cited

U.S. PATENT DOCUMENTS

| 4,264,990 A | 5/1981 | Hamas |
| 5,662,583 A | 9/1997 | Khouri |

(Continued)

FOREIGN PATENT DOCUMENTS

| EP | 1997457 A1 | 12/2008 |
| JP | 2003-504093 A | 2/2003 |

(Continued)

OTHER PUBLICATIONS

Extended European Search Report for European Applicaton No. 12744394.3, dated Dec. 9, 2015 (8 pages).

*Primary Examiner* — Yashita Sharma
(74) *Attorney, Agent, or Firm* — Finnegan, Henderson, Farabow, Garrett & Dunner, LLP

(57) ABSTRACT

A device for maintaining or achieving soft tissue expansion applicable to any body region already temporarily expanded including: an adhesive element deformable and capable of adapting to the shape of this body region, and which can then itself become mechanically rigid enough to resist tendency of the expanded tissue to recoil or to which a second material can be applied to form a stent adapted to the shape of the body area to provide the necessary structural rigidity to prevent recoil of the expansion and thereby induce its retention of its expanded shape after the stent is removed.

21 Claims, 9 Drawing Sheets

(58) Field of Classification Search
USPC ..... 623/7, 8, 23.64, 23.7–23.71; 600/38–41;
601/6–21; 128/897–899; 450/1, 39–81;
472/2.24
See application file for complete search history.

(56) References Cited

U.S. PATENT DOCUMENTS

| | | |
|---|---|---|
| 6,106,492 A | 8/2000 | Darcey |
| 8,496,702 B2 | 7/2013 | Rigotti et al. |
| 2002/0016129 A1 | 2/2002 | Khouri |
| 2004/0220505 A1 | 11/2004 | Worthley |
| 2007/0004993 A1 | 1/2007 | Coppens et al. |
| 2007/0028932 A1 | 2/2007 | Sampson |
| 2007/0057403 A1 | 3/2007 | Nielson et al. |
| 2008/0262400 A1 | 10/2008 | Clark et al. |
| 2009/0312746 A1 | 12/2009 | Khouri |

FOREIGN PATENT DOCUMENTS

| | | |
|---|---|---|
| JP | 2009-131534 A | 6/2009 |
| WO | WO 00/32084 A2 | 6/2000 |
| WO | WO 03/075750 A2 | 9/2003 |
| WO | WO 2008/116025 A2 | 9/2008 |

METHOD AND DEVICES FOR TISSUE EXPANSION

CROSS-REFERENCE TO RELATED APPLICATIONS

This application is a continuation of U.S. application Ser. No. 14/219,576, filed Mar. 19, 2014, which is a continuation of U.S. application Ser. No. 13/390,453, filed Sep. 19, 2012, now U.S. Pat. No. 8,821,573, which is a U.S. national-stage entry of International Application No. PCT/US2012/024782, filed Feb. 11, 2012, which claims the benefit of priority to U.S. Provisional Application No. 61/453,271, filed Mar. 16, 2011, and Italian Patent Application No. PD2011A000041, filed Feb. 11, 2011, which are herein incorporated by reference in their entireties.

BACKGROUND AND SUMMARY OF THE INVENTION

Despite great strides in cell culture technology and in the medical profession's ability to isolate stem cells and manipulate them to differentiate into various cell types, accomplishments in the field of tissue engineering solid organs remain limited.

This is because in addition to being a collection of specialized cells, a functional tissue engineered organ is generally thought to necessarily be capable to fulfill the following requirements:

1. Contain a scaffold within which the cells reside and organize themselves in the specific three dimensional architectural arrangement required for the organ to function. This scaffold is known in the art as the stromal component or the tissue.

2. Ensure that each individual cell in the organ remains within very close proximity to a capillary blood vessel that can supply it with the necessary nutrients. For this to happen, the construct needs to have a dense three-dimensional vascular network of blood vessels and capillaries.

3. Be able to connect this capillary network to the systemic circulation.

These three requirements constitute what is known in the art as the "Holy Grail" of tissue engineering. However, building in the laboratory a stromal scaffold with a functional capillary circulation connected to the arterial and venous circulation of the recipient remains an elusive goal.

Without a functional internal capillary network, current tissue engineered organs are generally limited to one or two cell layered constructs such as skin, cornea, blood vessels, and most recently urethras. The cells in these tissue engineered organs are generally not more than 1-2 millimeters away from the recipient circulation such that nutrients cart reach them by diffusion from the nearby endogenous capillaries of the recipient.

One known technique used to obtain the expansion of breast tissue without prosthesis implant, is called lipofilling and envisages the graft of adipose tissue (properly treated) into the breast that is to be expanded. The adipose tissue, after a suitable period (some weeks), gives mature fat cells fully integrated into the pre-existing tissue and makes the expansion of the breast essentially complete to result in a breast augmentation or a breast reconstruction in the case of a mastectomy. Even if the basic mechanism is not completely clear, it is supposed that such fat cells come from the transformation of mesenchymal stem cells present in the treated adipose tissue, favoured by the particular environmental conditions in which they are (see G. Rigotti, A. Marchi, M. Galie, G. Baroni, D. Benati, M. Krampera, A. Pasini and A. Sbarbati (2007) "*Clinical treatment of radiotherapy tissue damages by lipoaspirates transplant: a healing process mediated by adipose derived adult stem cells*". Plast Recon Surg. 119(5):1409-22; Rigotti G, Marchi A, Baroni G, Sbarbati A, Delay E, Rietjens M, Coleman S R (2010) "*Fat grafting to the breast: aesthetic and reconstructive applications*" In ed. Jones G E. Bostwick's Plastic and Reconstructive Breast Surgery, Third Edition, Quality Medical Publishing, 2010, pp 251-293; e Rigotti C, Marchi A, Sbarbati A "*Adipose-derived mesenchymal stem cells: past, present and future*" Aesthetic Plast Surg. 2009 May; 33(3): 271-3. Epub 2009 Apr. 21. PMID: 19381713 [PubMed—indexed for MEDLINE].

The treatment of the adipose tissue to be grafted in the involved body region is a known technique: the tissue fat is centrifuged and the fraction containing the vascular-stromal component is actually grafted. Alternatively, the fat harvested by liposuction can be allowed to sediment and the entire supernatant fat suspension used as the grafting material. This approach has several advantages, particularly when the graft is autologous, that is when the fat is taken from another body area of the patient. This technique makes it possible to obtain the elimination of any problem of rejection. In addition, other problems related to the use of prostheses are avoided, such as the risk of failure of the implant (breakage or other). Besides these advantages, the technique of lipofilling (that is the grafting of fat) has, however, some drawbacks, including the fact that the newly grafted fat tissue, before giving mature adipocytes well integrated into the surrounding tissue, may be at least partially absorbed into the body, reducing the effectiveness of the tissue expansion induced by the graft.

The inventors observed that this phenomenon is facilitated by the natural tendency of the expanded tissues to contract elastically to recover their original condition and therefore, have understood the need to support adequately the expanded body region in order to keep it in shape for the time necessary for the grafted adipose tissue to give rise to mature fat cells, that have stably taken root on the pre-existing tissue.

The invention as disclosed herein comprises a method of tissue engineering which is a radical departure from the prevailing wisdom in the art of trying to build an organ ex-vivo, in the laboratory (or in what is commonly referred to a tissue reactor), and then transplant it to the needy host. Also disclosed are several devices for achieving this method. The invention finds as one of its main applications in plastic and reconstructive surgery, in particular in the treatments necessary to achieve an increase in the volume of human breast, for example in mammary reconstruction and augmentation mastoplasty, although the invention has broader applications as well and should not be considered as limited thereto. For example, the method and devices disclosed herein also have application in the treatment of body contour defects, whether from scaring or congenital abnormality. Another application is in the expansion of solid organs as the expansion generates the scaffold or stromal component and the grafting provides the necessary cellular complement (whether obtained by liposuction or other harvesting and tissue culturing methods) required to regenerate the organ.

Previously disclosed in several of a co-inventor's earlier issued patents is a novel method and devices for performing the method of tissue engineering whereby the host organism is induced to generate in-situ this vascular stromal scaffold. As this vascular scaffold grows, it induces new blood vessel formation (neoangiogenesis) and derives its additional circulation from the host. MRI angiograms demonstrate that this method accomplished this tissue engineering crucial effect. This is disclosed and claimed in any one or more of one of the co-inventor's issued U.S. Pat. Nos. 5,536,233; 5,662,583; 5,676,634; 5,695,445; 6,083,912; 6,500,112; 6,514,200; 6,641,527; 6,699,176; 6,730,024; and 6,296,667, the disclosures of which are incorporated herein by reference.

External expansion as disclosed and claimed in these earlier patents achieved this effect by applying an external or "dynamic" orthogonal outward distractive pull against the surface of the tissues targeted to grow. The preferred methods and devices for achieving this external force application at the time was disclosed and claimed in the co-inventor's previous patents mentioned above, which are presently being successfully commercialized as the Brava Bra® device. At present, to the inventors' knowledge, this device is the only FDA reviewed external three dimensional tissue expander on the market. The Brava® device applies an external distractive pull on the outer surface of the targeted soft tissues by means of a controlled and continuous, relatively low, vacuum pressure. Although modifications of the vacuum pressure and intermittent cycling of the pressure to higher levels that cannot be tolerated for long periods was found to be a more effective method of expanding the organ.

Vacuum applies an isotropic force on the surface of the tissue, and its outward pull can be controlled through regulating the amount of negative pressure maintained in the dome shell. However, applying constant vacuum over complex and naturally moving surfaces is a challenge and the necessary device, while comfortable enough to achieve commercial success, is necessarily more cumbersome and difficult to wear and, while the inventors are unaware of any serious issues caused directly or indirectly by the use of this device, it must be acknowledged that it may, if not properly administered in accordance with the recommended regimen, exhibit a risk of problems for internal organs and for the surface upon which the device is applied.

Alternative means of applying a distractive force on an external organ such as the breast is to mechanically pull on the skin surface by pulling on an intermediate layer mechanically secured to the skin by means of an adhesive, or surface tension or sutures, or other mechanical fastening devices. Various examples of these devices may be found in the co-inventor's patents mentioned above.

In a presently pending U.S. patent application Ser. No. 12/298,011 filed Jul. 24, 2009 with a priority claim to Ser. No. 11/409,294 filed Apr. 21, 2006, the disclosures of both of which are incorporated herein by reference, there is a method disclosed for generating a tissue scaffold with external expansion by applying a vacuum followed by seeding the tissue scaffold with a suspension of fat cells obtained by liposuction and holding the enlarged expanded grafted space open to allow for successful engraftment. Also disclosed is the step of after injecting an expanded scaffold with more liposuctioned fluid volume, maintaining that further enlarged state for a certain period of time so that as the tension dissipates, the tissues stabilize and the graft revascularizes and survives.

Disclosed also is that to achieve this desired effect a Brava® bra-like external expander device could be used, or alternatively, a splint, bandage or other immobilizing device (hereinafter "splint" or "stent") could be applied that conformed to the new enlarged shape, adhered to the skin and was rigid enough to prevent any significant recoil, collapse or loss of the surgically engrafted expansion for a period of time.

As the inventors have continued their inventive activity during the course of their surgical practice, they have discovered that a splint or stent was more comfortable to wear than the Brava® device. Furthermore, compared to the Brava® device where wearing of the larger than ordinary bra was required for hours at a time, which translated to less than desirable patient compliance, a splint which is less cumbersome and more comfortable to the skin resolves the very important patient compliance issue.

As the patient's expanded scaffold is engrafted with "dilute lipoaspirate", the injected volume further enlarges the organ (the breast) and holds it in this enlarged state by means of an adhered, at least semi-rigid, splint that prevents recoil, this method not only helps the engraftment process, but can also cause further expansion.

As the procedure has been refined, more and more dilute lipoaspirate (more fluid, less fat cells) can be injected and more grafting sessions that were smaller in extent (less liposuction required) have been used. In between the grafting sessions, the semi-rigid conforming adherent splint is more comfortable, less discernible to others, and hence more likely to be worn than the Brava Bra® device. With this improved method, the need for using the Brava external expansion device between grafting sessions has been obviated, having been replaced by the less intrusive splint.

In further refining the procedure, to cause the organ to swell, instead of pulling on the outside for a long sustained period of time as originally performed with the external expander devices, physiologic fluid was injected inside the organ alone, without cells. The injection caused significant swelling and was limited by the internal tension inside the organ. In essence, injecting the breast with fluid produced the same effect as the external expander, i.e. tension in the breast. Left alone, the injected fluid would be expected to be rapidly reabsorbed by the body thereby simply reversing the expansion and reducing the swelling. Thus the tissue would not ordinarily be expected to sense any sustained tension that would induce the formation of a stromal matrix and recipient scaffold and the desired increase in volume obtained with the injection would be lost.

While working with the external expander and inflating breasts with physiologic solutions, the inventors came to the realization that the immediate application of the splint that retains the swelling maintains the sustained tension required for the tissue engineering matrix to form. Within a period of days to weeks, that sustained tension has been found to induce the formation of the stromal matrix in as effective manner to that of the sustained tension of the Brava external expander.

Internal tissue fibers under tension sense the same forces whether (under the effect of the Brava® device or other dynamic traction device) the skin surface is pulled from the outside or whether the skin is held up to prevent recoil once the internal tension has already been induced. From a mechanical standpoint the forces required for inflation of the tissue are thought to be approximately the same forces that will be forcing its recoil. The inventors therefore came to the conclusion that preventing the recoil of forced internal inflation by holding up the skin (forced inflation and passive splinting) achieves the same physiologic effect as pulling up on the skin to force its inflation (external dynamic expansion).

Interestingly, patients subjected to both modalities confirmed experiencing the same sensation.

While inflation is ideally diffuse if the inflating agent is placed throughout the tissue and within all tissue planes, it is also effective if the inflating agent is placed only in localized areas and we allow for natural diffusion of the injected material through osmotic forces and mechanical gradients of tissue compliance amongst the tissue types and the tissue planes. With respect to cellular agents injected into the tissue, such as fat, stem cells or the like, in order to achieve the best results with minimal necrosis, it has been found that diffuse injection of the inflating agent is preferred. For inflating agents that are acellular, such as saline, suspensions of particulate matters such as tissue matrix agents, or gels and other physiologically compatible fluids such as maybe even air (which has not yet been tried by the inventors but is conceived as eligible for use), it has been found that optimum results are not as dependent on a diffuse inflation.

The description above discusses inflating the soft tissue through injection of a physiologically compatible agent or fluid. While injection has been used by the inventors with success, the inventors conceive that the soft tissue can also be inflated through other means that can apply a distractive force to the tissues. One such example is to induce acute edema to the tissue and then while the tissue is expanded rapidly apply a passive stent. Using the breast as an example, a high pressure pump may be used to create a temporarily strong distractive force in cups applied to one or both of the breasts at pressures above what can be physiologically tolerated for more than a few minutes and then recycling after a few minutes rest giving time for the tissue to recover to achieve the desirable augmentation, remove the cups, and then apply passive stents to the breasts which are suitable for being comfortably and unobtrusively worn for some extended time period. Depending on the particular construction of the stent, and its ease of application (and expense), the inventors conceive that a patient could herself replace the stent to allow for personal hygiene, or return to the Doctor's office for another round of inflation and then another set of stents larger than the previous ones. In this way, the patient can take a stepwise expansion of her breasts until the desired size has beer reached.

In yet another modality, the Inventors are well aware of a low pressure bra-like device made and sold by Brava, LLC as one of the co-inventors is the inventor of that device. One of the issues which interferes with patient success in using the Brava Bra® is that of patient compliance. Although many patients are quite successful and are very happy with the results achieved with the Brava Bra®, some patients are not as diligent in their wearing of it as while it is remarkably slim and unobtrusive, it is yet more so than a thin bra cup. Furthermore, the recommended wear times are less than 24 hours a day, which gives the breast time to recoil and then when the Brava Bra® is reapplied, the starting size is less than when it was removed. The present invention of a passive stent may be coupled for use with the Brava Bra® in order to prevent breast recoil and thereby accelerate the augmentation process. Simply put, use of the passive stent for those times when the Brava Bra® is not worn transforms a sawtooth pattern into a stepwise expansion pattern of augmentation.

It is also contemplated by the inventors that the repeated inflation or distension of the soft tissue (breast as used for exemplary purposes only) may be achieved through a mixing of these various methods, in other words, the first inflation may be achieved through the creation of an edema or injection in the Doctor's office and subsequent inflations could be achieved through use of a low pressure or higher pressure cycling vacuum pump at home by the patient. It is also conceived by the inventors that a "kit" for home use could be put together comprising the presently commercially available Brava Bra® and vacuum pumps and a set of passive stents which the patient could self-apply during the intervals when not wearing the Brava Bra®.

In sum, the present invention is expected to be able to be used to maximize expected results through use of the Brava Bra® in soft tissue augmentation without surgical intervention or even injection.

When the patient returns back to the office, a few days to a few weeks after inflation, the splint is removed and the inventors have found that the organ (breast) has substantially maintained the operative enlargement due in large part to the adherent splint that prevented tissue recoil. However, while immediately after injection the breast was initially tight and firm from the large injection volume, it has been found after the passage of time to be soft and loose as the tissues had internally and externally stretched and expanded to accommodate the tension. In this regard, the physiologic process of tissue expansion has been found to be essentially similar to the dynamic external expanders.

With the enlarged (organ) breast now soft again, additional physiologic fluid may then be injected, enlarging it more until it becomes tight and firm again. A new splint may then be applied so that it conforms to the newly enlarged expanded state and the patient is then free to return to their normal activities, wearing this rigid splint as an adherent bra cup for the few days to weeks as required fox the tension to equilibrate as the tissues expand further.

The process may then be repeated a few times until the desired recipient scaffold size is reached. At that point, the graft is diffusely dispersed inside the expanded scaffold and a new splint is applied to allow the grafts to revascularized and successfully engraft to regenerate the deficient organ.

Alternatively, this process of physiologic solution injection to expand the tissues followed by passive splinting to maintain the expanded state can be serially repeated until mechano-transduction, the process through which tissues grow in response to sustained mechanical expansion, generates enough tissue to obviate the need for tissue grafting. In essence, the inventors discovered a new method of tissue expansion which, in effect is an alternative to the devices described in previous patents and patent applications.

It is thus one aspect of the present invention to create a physical structure to be applied to a body area subject to tissue expansion, which is structurally and functionally designed to overcome the limitations described above with reference to the cited state of the art. In this regard, one function of the invention is to provide a device for maintaining morphology of a soft tissue site or organ, i.e. that is able to maintain the shape and volume of the body area subject to expansion, and to counteract any natural tendency to contract by the involved tissues.

Another desirable feature of a preferred embodiment of the invention is to provide such a device that is immediately usable in a post-operative phase and which also exhibits a high biocompatibility with the skin, in order to permit it to be safely and comfortably worn for a period of 2-3 weeks. Yet another desirable feature of a preferred embodiment of the invention is to provide such a device that is lightweight and easy to carry, in order to encourage its being worn by the patient during normal daily activities and thus improve patient compliance. Still another desirable feature of a preferred embodiment of the invention is to provide such a device that is readily customizable (malleable) so as to be able to more fully adapt to the shape of the body area of the individual patient. Yet another desirable feature of a preferred embodiment of the invention is to provide such a device that is easy to apply to the involved body area and, if necessary, just as easy to replace.

The invention also comprises a kit that can contain a device to distend the breast, such as a vacuum pump of the Brava modality or a high pressure pump, one or more breast cups to be applied to the breast to achieve the distention, and one or more passive splints which could potentially be applied over several weeks by the patient herself.

It will be apparent to any person of ordinary skill in the art of surgical reconstruction that one of the invention's preferred embodiments comprising the splint to be applied over the breast (organ) can be embodied in a multitude of designs using a large variety of materials.

The common requirement however to these are as follows:

Important Attributes:
  a. adheres firmly to the skin or the surface of the organ to prevent recoil and detachment during the patient's regular activities.
  b. can be conformed to match and cover the exact shape and contour of the swollen breast or organ.
  c. while malleable when first applied, it should rapidly harden to espouse the desired shape.
  d. in the hardened state have mechanical properties that can counteract the tissue recoil.
  e. be bio-compatible and capable of being tolerated for long term application (1-3 weeks of uninterrupted wear). The splint is conveniently adapted to be made out of many bio-compatible "breathable materials" as known in the art.

Desirable Attributes:
  a. easy to apply kit
  b. comfortable (semi-rigid, that is while preventing collapse, rubber like to allow for some bending, as compared to rock hard plastic)
  c. thin (one Inch or less)
  d. skin colored
  e. smooth contours that blend and taper with the chest wall skin
  f. have the appearance of a stick on, well camouflaged external breast prosthesis.
  g. items b-f should render the device easy to conceal and to wear 24/7.
  h. transparent or translucent so the underlying skin can be monitored, both to ensure that the splint is in good adhesive contact at the time of application and that any rash or irritation can be readily detected.

Another way of mechanically coupling the splint to the skin is surface tension. Surface tension is the naturally occurring means by which the body holds together tissues that need to remain mechanically coupled but yet glide and avoid shear forces. This is how the expanding rib cage transmits the mechanical force of inhalation to the soft sponge like lungs to expand and this is how bowel loops can glide past another while held together too.

The external splint can be akin to a swim cap or to a toilet plunger pump. Semi-rigid, conforming and with a film layer of surface tension that transmits the mechanical recoil of the plunger rubber to the skin surface and pull it outward.

The many embodiments of this splint embodiment (or adherent semi-rigid, conforming bra cup) that can be applied over an organ swelled up and tensed up by injection include but are not limited to:

A. Single Layer Embodiment:
  Here a spray, paint, or putty form of a soft rubber or a rubber sheet is applied over the surface of the organ and that material cures to become rigid enough to prevent recoil. It could be adherent by itself or might require the addition of an adhesive glue such as a biologically tolerated adhesive or use surface tension. It might include imbedded or subsequently applied reinforcing fibers that contribute to the desired mechanical characteristics.

Specific embodiments would include:
1. The hair spray like device: an aerosol delivered spray of a plastifying material that can coat the surface of the organ and rapidly dry or cure to become an exoskeleton-like shell structure that is hard enough to prevent the forces of recoil. This might be achieved by a modification of the current colloid dressing solutions or the liquid band aids or the cyanocarylate glues used for wound closure or other biocompatible polymers that can offer the desired characteristics.
2. Materials similar to the above, instead of being sprayed could be painted or smeared over the surface of the organ where they would rapidly cure to become a hard shell that espouses its exact swollen contour and prevents it from recoiling. A solvent can then be used to remove it when needed.
3. A putty-like soft rubber that can be spread over the surface and made to cure and become hard either with a catalyst or on air contact or by varying the temperature or by UV light exposure. The material can be delivered as sheets that are inherently tacky and stick to the surface when applied, or that need a priming sticky layer like a tissue glue to be applied first and then the confirming rubber putty adheres to that glue. Examples of these materials include the cyanoacrylates, epoxy, acrylic, urethane or other polymers such as silicone based medical adhesive glues.
4. A sheet of adhesive tape like material. This can be either a textured or fibrous material or it can be a foamy or porous material that is taped over the surface of the organ. There are many well-tolerated pressure sensitive adhesive compounds that can provide a firm adhesion between that tape or sheet and the skin. The adhered sheet or tape can then become hard either because of its inherent ability to cure on exposure to air or water or with the help of a catalyst, temperature changes or UV exposure. The device would be supplied in an air tight pouch ready to be applied and would cure either by itself on exposure to air or water, or with the help of the necessary catalyst. Alternatively, the device can be made to harden by painting it, spraying it or adding to it a plastic, rubber, fiberglass, epoxy, urethane or other biocompatible polymer, even a plaster of Paris like material.

B. Two layered embodiment: First apply over the breast or the organ a layer of material that will adhere to the skin or to the surface of the organ to be enlarged. This must be a material known to be well tolerated for prolonged surface contact (this can range from adhesive tape to hydrogels and hydrocoloids, to cyanocarylates and other liquids or gels that stick to the tissue surface). Then add to this another layer of a material that can be made to adhere to the first layer, be malleable to precisely espouse the contour of the swollen organ, and that can be made to cure and become rigid in this new shape and form (this can range from thermoplastics to fiberglass like tape to plastics that can be cured on air or water contact or with the help of curing agents, catalysts, or temperature or UV light, to rubbers and other biocompatible polymers such as silicone and/or polyurethane and their related products and derivatives.

Specific embodiments would include:
1. an adhesive hydrogel for the first layer and then glued and stuck to it.
   a. a thermoplastic material added for rigidity and made to adhere to the hydrogel.
   b. fiberglass like material added for rigidity and made to adhere to the hydrogel.
   c. plaster of Paris-like material added for rigidity and made to adhere to the hydrogel.
   d. a natural or synthetic polymer or their derivatives capable of adhering to the hydrogel and be malleable enough in the first state to conform to the surface contour and become rigid in the second state to prevent recoil.
2. An adhesive silicone gel for the first layer and a rigidifying silicone putty adhered to it for the second layer. That putty might contain a fibrous mesh as a rigidifying framework.
3. An adhesive foam for the first layer and then glued or stuck to it:
   a. a thermoplastic material added for rigidity and made to adhere to the foam
   b. fiberglass like material added for rigidity and made to adhere to the foam.
   c. plaster of Paris-like material added for rigidity and made to adhere to the foam.
   d. a natural or synthetic polymer or their derivatives capable of adhering to the foam and be malleable enough in the first state to conform to the surface contour and become rigid in the second state to prevent recoil.
4. An adhesive biocompatible sheet like Tagaderm® or OpSite® or a woven or knitted material similar to the Second Skin.
   a. a thermoplastic material added for rigidity and made to adhere to the breathable material adherent to the skin.
   b. fiberglass like material added for rigidity and made to adhere to the breathable material adherent to the skin.
   c. plaster of Paris-like material added for rigidity and made to adhere to the breathable material adherent to the skin.
   d. a natural or synthetic polymer or their derivatives capable of adhering to the breathable material adherent to the skin and be malleable enough in the first state to conform to the surface contour and become rigid in the second state to prevent recoil.

Anyone of ordinary skill in the art, given the teaching herein, can also understand that in 1-4 above, the first layer that is conforming, biocompatible and adhesive can be subsequently made rigid by adding to it chemical compounds that can provide it with the desired mechanical rigidity.

5. Biocompatible Materials that can be used:
   Natural polymers and their derivatives such as Nitrocellulose, Chitin, etc.
   Synthetic polymers such as polycarbon, polyvinyl, polyurethane, polyesther, silicone, and their derivatives.

C. Multiple layer sandwich: First an adherent layer (same range of materials as above) then a rigidifying layer (same range of materials as above), then a final layer that camouflages the entire construct.

The disclosed invention may also be used for a method of three dimensional tissue expansion.

In conventional tissue expansion, inflatable silicone shells are surgically inserted and after the surgical wound heals, the expander is serially filled with physiologic fluid to distend it. ultiple filling sessions a few days to a few weeks apart compress the intervening tissues between the skin surface and the expander shell and only expand the surface envelope. When removed these expanders then leave behind a cavity, a dead space that needs to be collapsed if the expansion is used for tissue coverage or in the case of breast reconstruction replaced with an inert foreign material implant.

With the present invention of tissue expansion, there is no surgical intervention required to insert any device. By simply injecting a physiologic fluid inside the organ to be augmented, by inducing an edema, or otherwise mechanically deforming it, not only is the envelope generated and stretched, but what does occur is that a stromal three dimensional recipient matrix for tissue engineering is also generated. As with conventional expansion, the quantity injected is limited by the level of tissue tension that can be tolerated and repeated injections are preferably needed a few days to weeks apart, or once the tissues expand and become lax again to become eligible for further injections. However, while with the internal expanders tension is maintained by the distended shell that compresses the underlying tissue and only stretches the outer envelope, with the present invention the tension on the tissues is generated by the application of an external shell that prevents collapse and uniformly distributes the tension to all the tissues contacting the splint to induce their uniform expansion. With the present invention using the splint, no surgery is required, no complication can result front foreign material being inserted, no tissue compression at all. Only diffuse generalized internal expansion forces (tension) are created, which have been found to be adequate to achieve the desired effect.

Other examples of suitable injectable materials range from simple physiologic electrolyte solutions to dilute suspension of specialized cells, to solutions containing growth promoting agents, or to suspensions and solutions of tissue matrix components that might altogether obviate the need for the cell seeding step as the improved injectate stimulates not only stromal matrix formation but also the proliferation of cells required to populate the organ.

As for the preferred embodiment, the inventors continue to search for new materials which satisfy both the important as well as the desirable attributes. However, at the time of filing, the inventors have successfully used the process of applying a layer of surgical tape, microfoam or hypofix type, and added on top a layer of fiberglass material customarily used to make fracture casts. While it is still malleable, the fiberglass plastic can be made to stick to the tape while it rapidly cures into a hard shell (like a cast) that espouses the contour of the expanded breast. This hard cup bra-like splint then remains adhered to the tape which is itself adhered to the skin. If well applied, the inventors have found that this construction will hold for a week, however the inventors would prefer other materials that would exhibit a longer life. This construction results in a somewhat cumbersome device but does have the advantage of being made out of off the shelf materials routinely available to any surgeon.

While not to be considered as limiting in any way, or as fully and completely defining the scope of the inventions disclosed herein, the inventors shall further exemplify the invention through the illustrative description and drawings depicting the preferred embodiments.

DEFINITIONS

It should be noted that in the present description and following claims, an element will be called "deformable" or "malleable" if its shape can be changed even under the effect of negligible forces, such as those expressed by a simple manipulation of an operator, particularly when it can be manually morphed to the shape of a human breast or other organ or other contour defect in need of correction. Malleable would include a moldable or shapeable sheet of material or sheets of material such as fiberglass or plaster of Paris impregnated cloth which is initially shapeless and adopts the morphology of the body tissue to which it may be closely applied. In addition, an element will be called "rigid" or "semi-rigid" when it will not deform significantly due to typical stresses caused by morphological forces such as the natural contraction of a distended breast, which is expanded by for example injecting a physiologically compatible fluid, inducing an edema such as by applying and cycling a high pressure vacuum to the breast, by applying a continuous low pressure vacuum over time (such as under pressures recommended for use with the Brava Bra®), etc. Furthermore, in the description and subsequent claims, the deformation of an element will be called "not appreciable", when, conformed to the shape of the tissue desired to be enlarged, such us by having the shape of a cup similar to a human breast, and undergoing a load of radial compression, produces a not meaningful volumetric shrinkage which materially detracts from achieving the desired tissue expansion.

As used herein, the term "physiologically compatible agent" or "physiologically compatible fluid" should be understood as including both "cellular agents" or "cellular fluids" such as stem cells and fat, as well as "acellular agents" or "acellular fluids" such as saline, gels, air, etc. Cellular agents or cellular fluids are understood as an agent or fluid that principally comprises cells, stem cells, harvested cells, genetically manipulated cells, cultured cells or the like. Acellular agents or fluids are understood as comprising gels, suspensions or solutions such as saline, chemicals that might promote growth or stabilization or tissue health, biologic tissue promoters or tissue substitutes, tissue inductive material, tissue matrices, etc.

As used herein, and elsewhere, the words "splint" and "stent" are used interchangeably but both can be defined as a deformable or moldable device intended to be shaped to be in intimate contact with the skin or other soft tissue surface and which maintains the morphology of the surrounding and underlying tissues. The word "splint" is generally considered is being relatively rigid in orthopedic uses while a "stent" is generally considered as being deformable or moldable to more closely follow the contours of the surface in question. The desirable properties of the stent or splint as described herein characterize the device being referred to so as to enable those of ordinary skill in the art to understand this reference.

The term "passive splint" or "passive stent" or "splint" or "stent" as used herein shall be understood as meaning a device which does not apply an external force to any underlying tissue to which it might be adhered, other than to resist the natural morphological forces which seek to return soft tissue to its previous relaxed or natural state. It is to be contrasted with what might be referred to as a "dynamic" force application device, such as a vacuum pump, which has the capability to apply an external force to body tissue.

BRIEF DESCRIPTION OF TIE DRAWINGS

Figure 3:
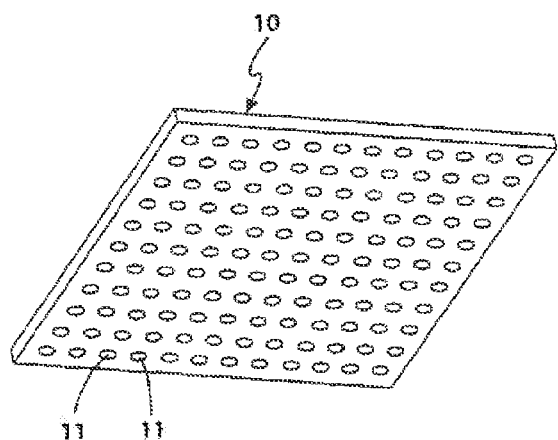
Figure 4:
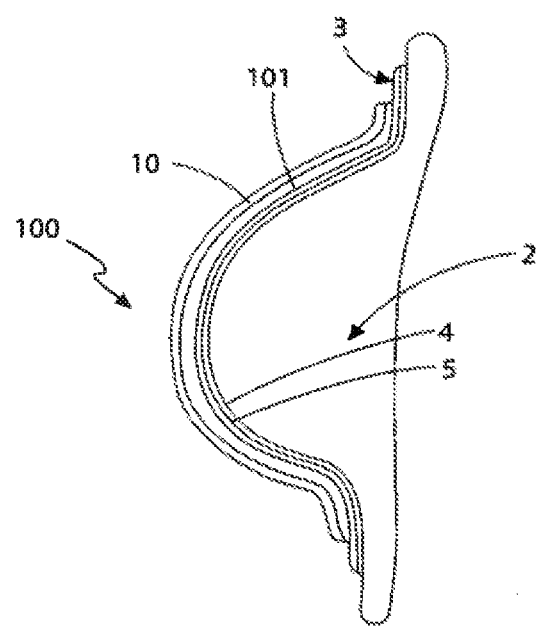
Figure 5:
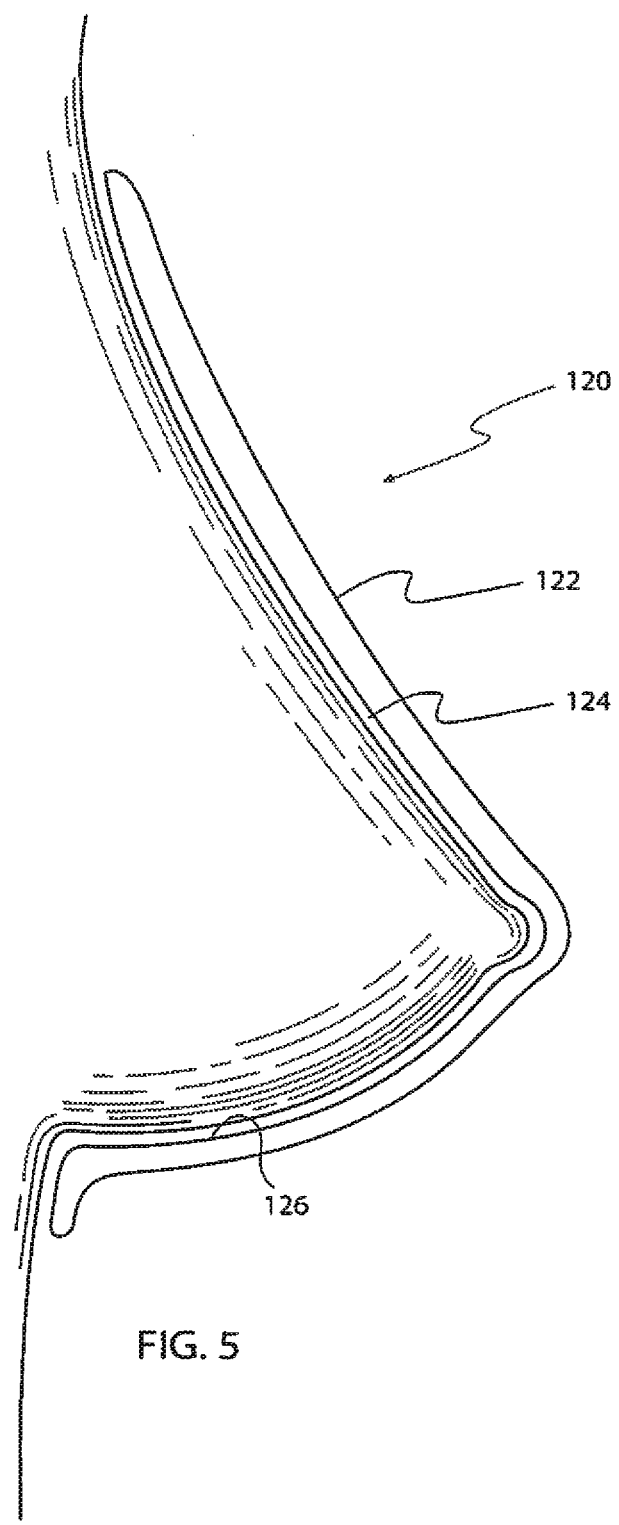
Figure 6:
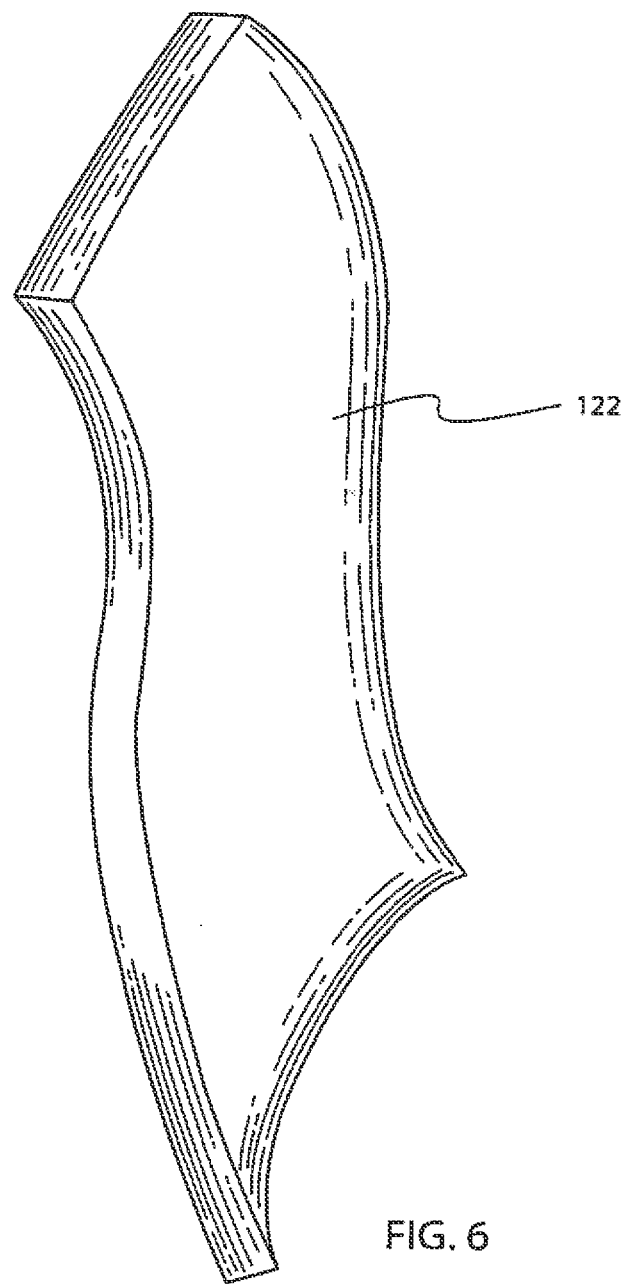
Figure 7:
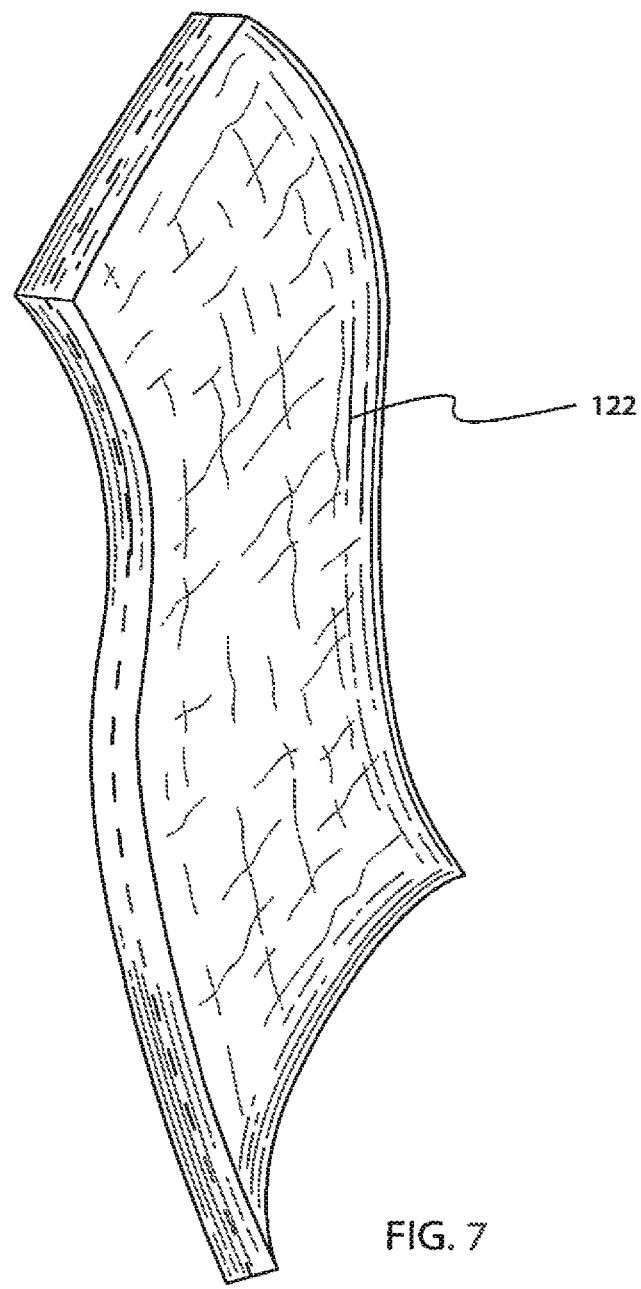
Figure 8:
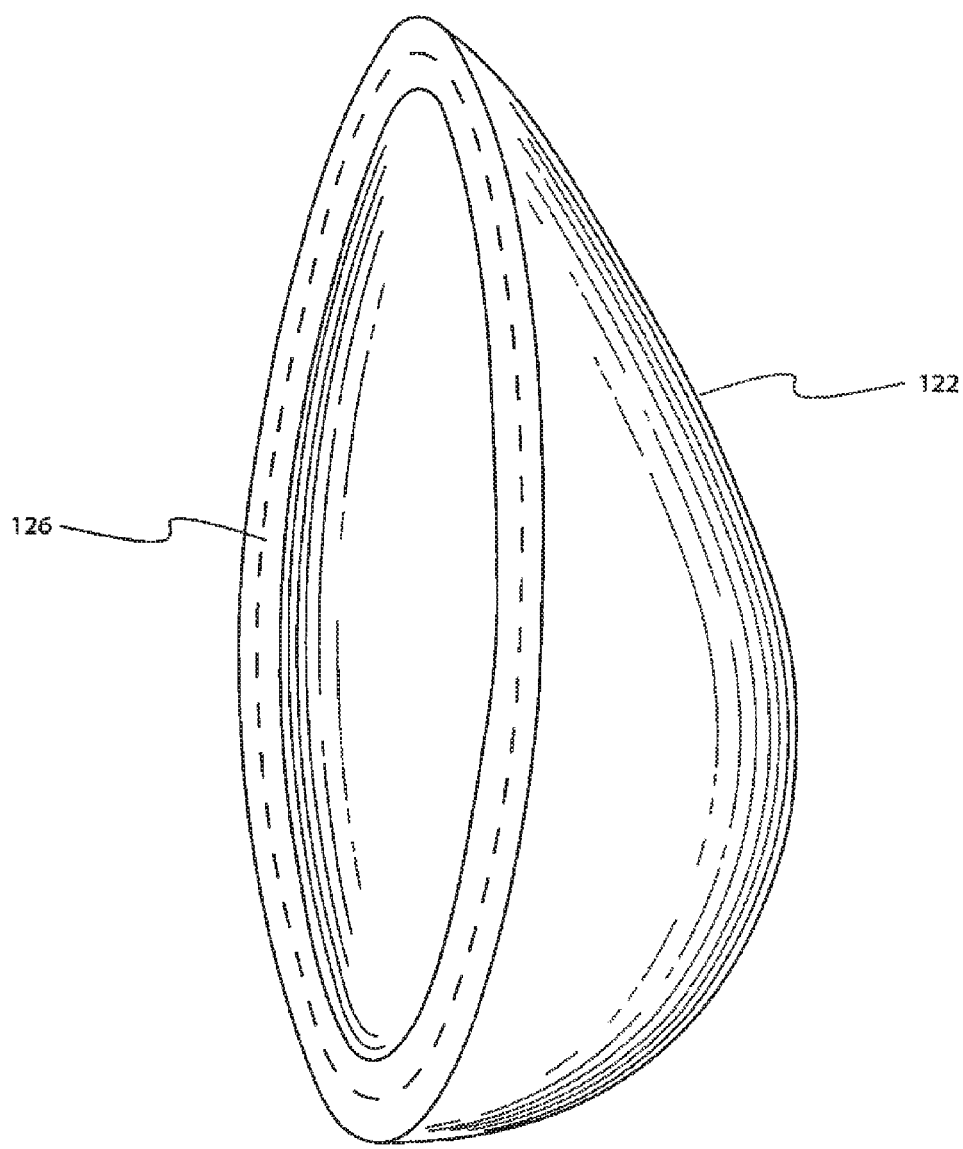
Figure 9:
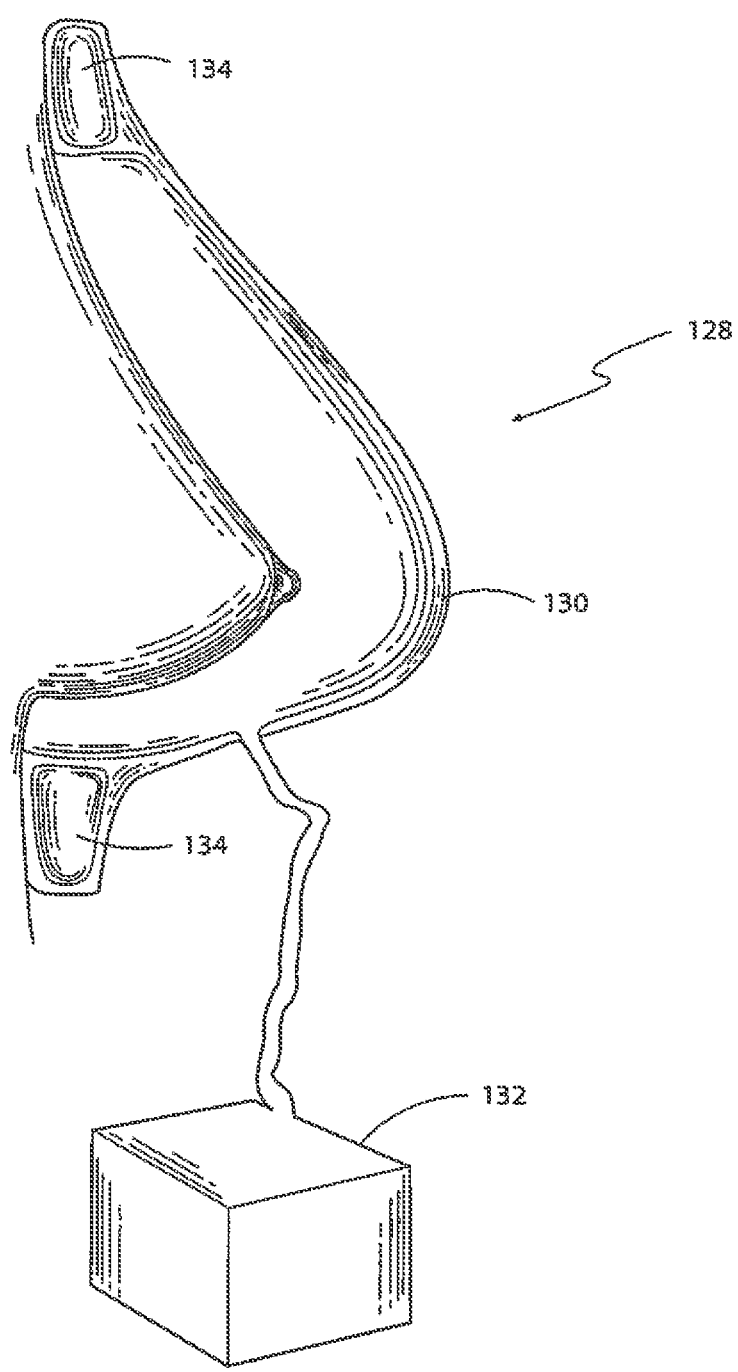
Figure 10:
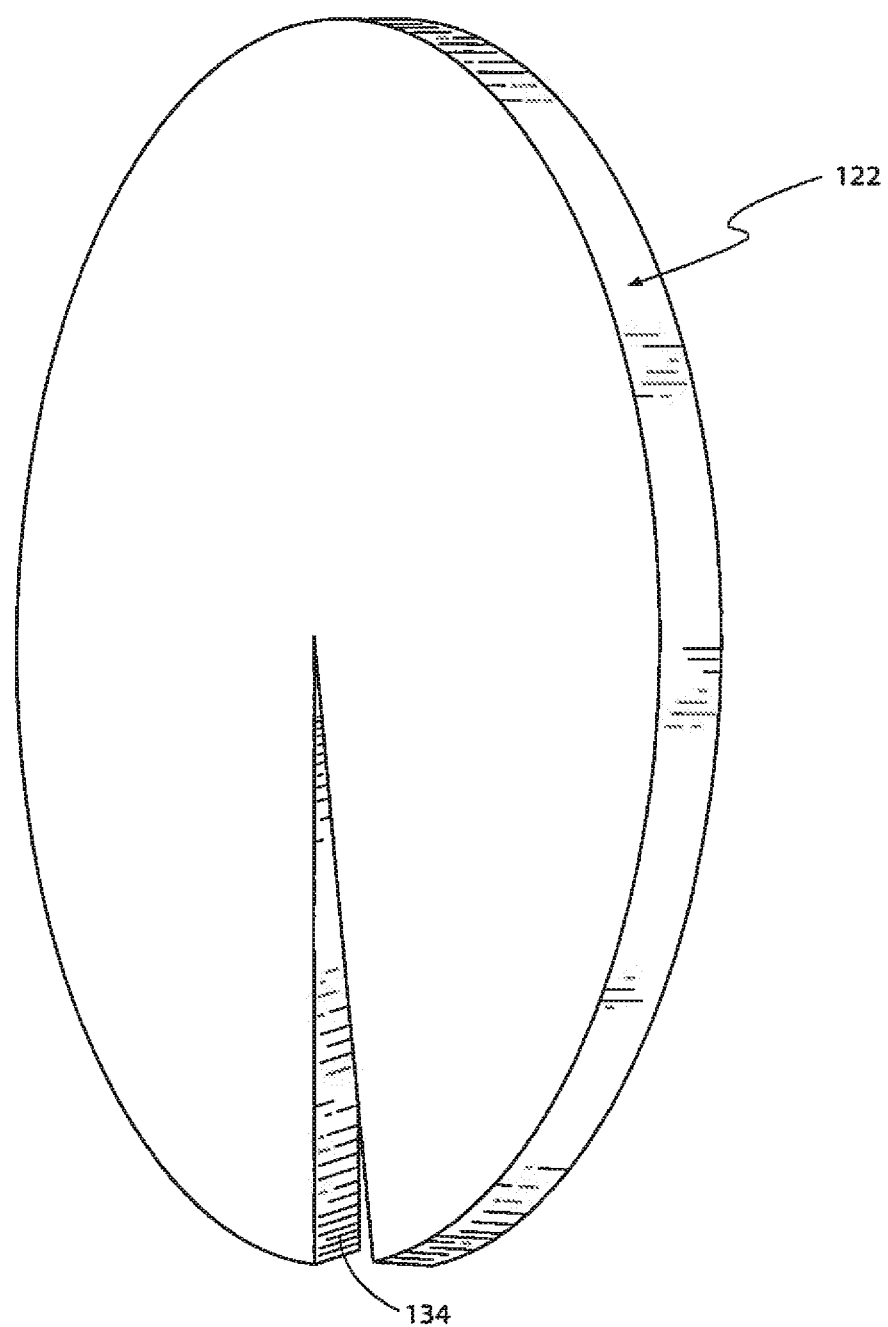
Figure 11:
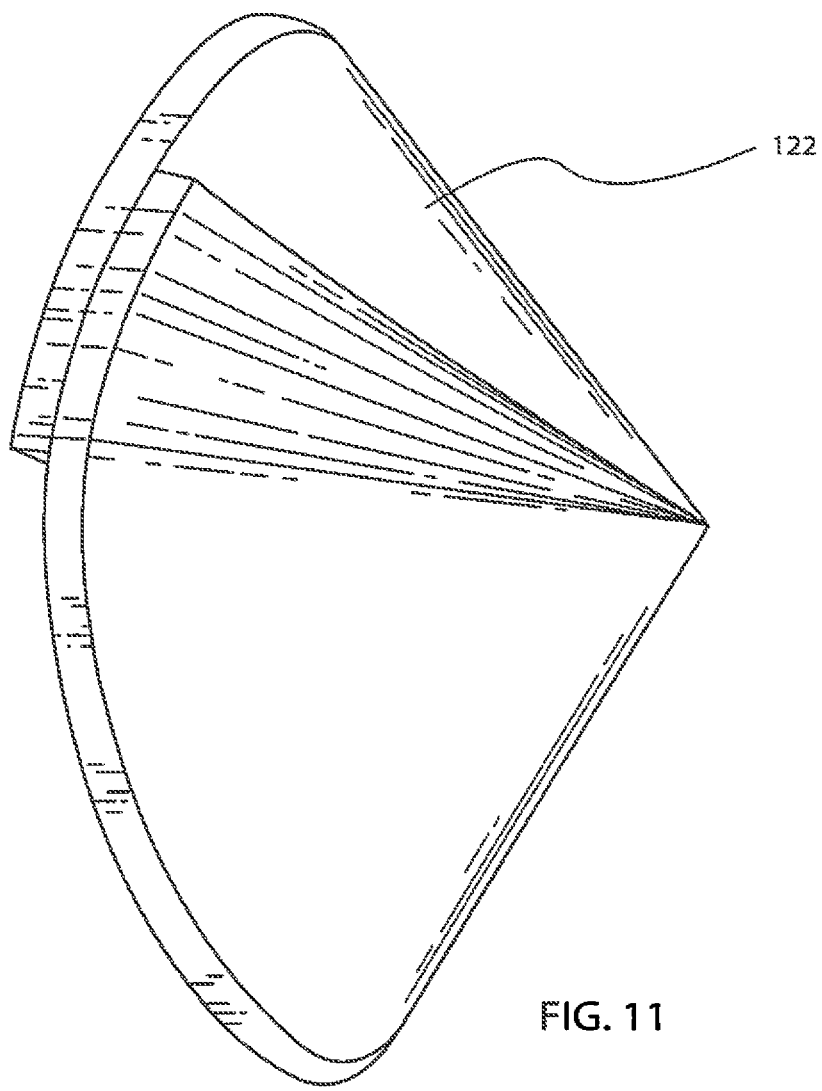

FIG. 3: is a perspective view of a second sheet of material, adhered to the first and adjustable between deformable and rigid in character;

FIG. 4 is a cross-sectional view of a second embodiment of the invention, applied to a breast subject to tissue expansion;

FIG. 5 is a cross-sectional view of another embodiment of the invention comprising what can be a single or multiple layer splint, applied to a breast;

FIG. 6 is a perspective view of another embodiment of the invention comprising a malleable sheet;

FIG. 7 is a perspective view of yet another embodiment of the invention comprising a malleable sheet which may be woven or reinforced;

FIG. 8 is a perspective view of yet another embodiment of a splint that may be pre-formed in the approximate shape of a breast;

FIG. 9 is a perspective view of a vacuum pump connected to a bra cup for inducing an edema to thereby distend the breast;

FIG. 10 is a perspective view of yet another embodiment of the invention comprising a splint formed in an approximate circular pattern with a slit for being folded over onto itself and creating an approximate cone shape; and FIG. 11 is a perspective view of the cone-shaped splint formed with the circular shaped splint shown in FIG. 10.

DETAILED DESCRIPTION OF THE PREFERRED EMBODIMENT

Figure 1:
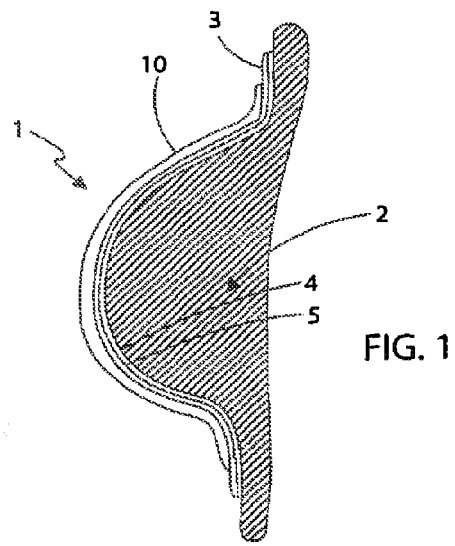
FIG. 1 is a cross-sectional view of a first embodiment of the invention comprising a stent or dome applied to a breast previously subjected to tissue expansion.
Figure 2:
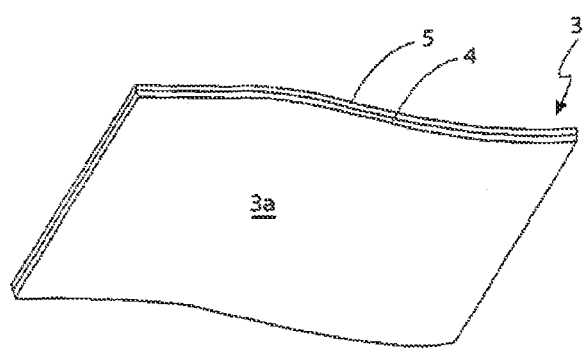
FIG. 2 is a perspective view of a sheet shaped adhesive element to be adhered to the breast and conform to its shape.

With reference to FIGS. 1 to 3, the first embodiment is generally referred to as 1. The device (1) is intended to be applied to the soft tissue body area subject to tissue expansion. In this instance, and for illustrative purposes only, the body area consists of a breast (2) whose volume was increased, preferably by injecting a physiologically compatible fluid such as saline, or less preferably by grafting properly treated autologous adipose tissue, in each instance optionally preceded by a period of treatment of vacuum or mechanical stimulation. Nevertheless it is understood that the present invention can be applied in the same way in any surgery, aimed at changing the congenital or acquired body profile through fluid injection or adipose tissue graft, such as in the treatment of depressions caused by scars, surgical resections or malformations. The device is not only limited to external skin surfaces but can also be applied to internal defects and to solid organs.

The device (1) preferably includes a sheet-like layer of an adhesive element (3), which is preferably made from materials that are easily deformed even at room temperature (about 25° C.) and able to adapt to the widely varying shapes and sizes of the female breast (2). The adhesive element (3) is preferably sheet-shaped, and includes, in correspondence of its outer surface (3a), an adhesive layer (4) that may be applied directly on the skin surface of the breast (2), and a backing layer (5) superimposed to the adhesive layer (4). Both layers (4) and (5) may preferably have a thickness between about 0.5 and 3 mm. The adhesive layer (4) is preferably an hydrocolloid, with high biocompatibility with the skin, so to ensure that the device (1) can be safely and comfortably applied to, and worn on, the breast (2) for reasonably lengthy periods of time, if necessary, without needing replacement. In addition, the biocompatibility of the adhesive layer (4) allows its application on the skin immediately after the surgical breast expansion, even in the presence of post-operative edema which is typically present after these surgical interventions.

The backing layer (5) is preferably made of soft polymer material, e.g. thermoplastic polyurethane based foam or other polymeric material with similar characteristics of softness and deformability. In this way, the adhesive element (3) can adhere completely to the skin surface of the breast (2), adapting virtually perfectly to its shape. The adhesive elements described above may be provided for example by the company Convatec under the trade name of DuoDerm®.

The device (1) also preferably includes a structural element (10) coupled to the opposite side of the adhesive layer (4). Even the structural element (10), like the adhesive element (3), is preferably sheet-shaped, with a thickness preferably between 0.5 and 4 mm. The structural element (10) is preferably basically rigid at room temperature, so that it does not deform significantly when subjected to stresses caused by the natural contraction of the body area involved in the tissue expansion. In particular, the structural element (10), at room temperature, is preferably able to resist without deforming significantly when loaded by the natural contraction of the expanded soft tissue, such as the breast (2), following tissue expansion and, among other factors arising from the tissue elasticity and from the post-operative reabsorption of the edema. The material preferably used for the structural element (10) exhibits a high chemical compatibility with the material used for the backing layer (5) of the adhesive element (3), so that it can ensure an effective adhesion to it, even without additional layers of glue. However, it is optionally envisaged that an additional adhesive layer can be applied between the two elements 3 and 10, for example a cyanoacrylate-based material indicated for medical use. Most preferably, the structural element (10) is made of thermoplastic polymer having properties such that when heated to a temperature between 50° and 80° C. (at first instance comparable to the melting point of the polymer), it softens in such a way to be easily deformed by a surgeon's manual manipulation. In this way, the structural element (10) can be stretched over the adhesive element (3), be adapted perfectly to the shape of the breast (2) and maintain this conformation.

Thermoplastic polymer materials softening at temperatures above 80° C. are not presently considered suitable for use in the present invention, because they would be too hot to be manipulated by a surgeon or to be used on a patient, even in overlap with the adhesive layer (3). On the other hand, thermoplastic polymer materials softening at temperatures below 50° C. are not presently considered suitable for use in the present invention, because they would not have adequate stiffness at room temperature or at temperatures between 35 and 40° C. easily accessible in many countries in summer. Preferably, the structural element (10) is made of a polymer based on polycaprolactone, covered with a layer of urethane acrylates. Several holes with a diameter ranging between 3 and 5 mm are made preferably on the structural element (10) and placed regularly on its surface. These holes (11) allow an easier deformation of the structural element (10) when brought to temperatures between 50 and 80° C., allowing at the same time a decrease of the mass of the structural element (10), in order to be lighter and to provide faster and more even temperature changes both in the heating and the cooling phases.

The use of this preferred embodiment takes place as described below, at the end of the treatment of tissue expansion of the soft tissue, preferably obtained through the injection of physiologically compatible fluid or grafting of properly treated autologous fat tissue. In the first phase, the adhesive element (3) is carefully laid on the expanded breast (2) to adhere perfectly to the skin surface. After that, the structural element (10) is heated at a temperature between 50 and 80° C. so that the surgeon can easily deform ii and lay it on the adhesive element (3) previously applied to the breast (2), adapting to its morphological conformation. The preferable chemical compatibility between the adhesive element (3) and the structural element (10) permits their mutual adhesion. Both the adhesive element (3) and the structural element (10) are laid to cover the entire area involved in the tissue expansion, including preferably a considerable margin around it. The structural element (10) cools rapidly to room temperature, making it stiff enough to hinder effectively the natural tendency to contract of the expanded tissue.

The sizing and the material of the structural element (10) are such that the cooling takes place as quickly as possible, but long enough to provide the surgeon with the time necessary to lay the structural element on the adhesive element (3). After the application of the structural element (10) and its cooling, the device (1) can be left on the breast (2) for a long period, even weeks if considered desirable, to promote the development of mature fat cells and their integration into the pre-existing tissue. If necessary, the device (1) can be replaced, by detaching the adhesive layer (4) from the breast (2) and repeating the steps described above with a new adhesive element and a new structural element. The device of the present invention is very lightweight and easy to wear, without causing discomfort or pain in the body region around the expanded tissue (breast). In fact, the pressures caused by the tissue's natural contraction is very low, in particular if compared with those necessary to stimulate its expansion by vacuum application as in the known devices. In addition the device of the present invention is customizable, as it is adaptable to the morphology of the specific patient. A further advantage of this invention is that its application promotes a biological response, which is thought to lead to the transformation of the stem cells present in the treated and grafted adipose tissue into mature adipocytes. The structural element (10), before being used, can be provided in the form of a flat sheet or in a convenient alternative, already preformed cup according to different predetermined sizes.

With reference to FIG. 4, another embodiment of the invention is shown and referred to generally as 100 therein. The device 100 differs from device 1 described above by incorporating an additional element with variable thickness 101, interposed between the adhesive element (3) and the structural element (10). The function of this element with variable thickness (101) is to improve the adaptability of the structural element (10) to the morphology of the expanded body region through a controlled reduction of its volume and thickness.

The element (101) designed with variable thickness is preferably made of polymer foam, e.g. polyurethane, whose radial thickness is adjusted by aspiration of the air contained in it.

Yet another embodiment 120 is depicted in FIG. 5 and includes within this single drawing figure a number of alternative constructions. For example, there is depicted a stent 122 which has been adhered to a breast with an adhesive layer 124. Stent 122 could have the layer 124 of adhesive applied to its inner surface 126, or the adhesive could be applied separately such as by being sprayed on or as being part of a double-sided, adhesive coated tape 124. Layer 124 could be a layer of gel or silicone and if necessary an additional layer of adhesive could be applied. Layer 124 could also be a layer of second skin. The single layer stent 122 could be formed from a sheet of material (see FIGS. 6 & 7) such as a thermoplastic material, natural or synthetic polymer or from multiple sheets of overlapping material which cures into a rigid construction, like fiberglass or plaster of Paris as might be used for a cast, for example. Stent 122 could also be applied like a putty, such as silicone. There are many other materials, as known to those of skill in the art which could be substituted for these exemplary materials, using the teaching and guidance of the present disclosure.

As shown in FIG. 6, the stent 122 may be a single sheet of material before application to the soft tissue site; flexible for being readily conformed to the soft tissue site and then being capable of becoming rigid to maintain the morphology of the site. For example, such a flexible single sheet of material 122 may be sized to adequately cover the breast and as explained above have one of its surfaces covered with adhesive or not. As shown in FIG. 7, the stent 122 may be woven or reinforced which can make it both easier to pre-mold into shape and also better hold its molded shape after it is cured or otherwise transformed into a rigid structure adhering to the breast. FIG. 8 depicts yet another representative shape for the stent 122. As shown therein, the stent 122 may be pre-molded into somewhat the shape of different breast cup sizes to minimize the possible introduction of wrinkles as the stent 122 is manipulated around the breast. Also, optionally, a flattened edge surface 126 to help form a seal at the edge of the stent 122 against the patient's chest.

As shown in FIG. 9, a Brava Bra® system 128 may include a breast cup 130 adhered around a breast and held in place by a vacuum created between them by a pump 132. The periphery may also have an adhesive applied to help hold it in place during wearing. Pump 132 could be either a low pressure pump for continuous use in accordance with the recommended protocol, or a higher pressure pump for recycling as explained above to distend the breast.

As shown in FIG. 10, the splint or stent 122 may be pre-formed in an approximately circular shape with a slit 134 to facilitate its being folded or collapsed around itself and thereby form the cone shape shown in FIG. 11.

The methods of use of the various inventions disclosed herein have been explained above as would be readily understood by those of skill in the art.

The invention has been illustrated through its preferred embodiments as shown in the drawing figures and as described in the description above. These preferred embodiments are not intended to be limiting in any way. Instead, the invention is intended to be limited solely by the scope of the claims appended hereto and their equivalents.

What is claimed is:

1. A method for augmenting an organ, comprising:
   transitioning the organ from a first state to a second state, wherein the organ envelops a first volume in the first state and envelopes a second volume in the second state, the second volume being greater than the first volume; and
   affixing a passive stent to an outer surface of the organ when the organ is in the second state;
   wherein the passive stent maintains the organ in the second state.

2. The method of claim 1, wherein the organ is an external organ.

3. The method of claim 1, wherein the organ is a breast.

4. The method of claim 1, wherein the organ is an internal organ.

5. The method of claim 1, wherein transitioning the organ from the first state to the second state includes injecting a physiologically compatible agent into the organ.

6. The method of claim 5, wherein the physiologically compatible agent is derived from adipose tissue.

7. The method of claim 1, wherein transitioning the organ from the first state to the second state includes injecting an acellular agent into the organ.

8. The method of claim 1, wherein transitioning the organ from the first state to the second state includes injecting a tissue matrix agent into the organ.

9. The method of claim 1, wherein transitioning the organ from the first state to the second state includes injecting a growth-promoting agent into the organ.

10. The method of claim 1, wherein transitioning the organ from the first state to the second state includes grafting adipose tissue into the organ.

11. The method of claim 1, wherein transitioning the organ from the first state to the second state includes applying vacuum pressure to the organ.

12. The method of claim 11, wherein applying vacuum pressure to the organ includes applying a constant vacuum pressure to the organ.

13. The method of claim 11, wherein applying vacuum pressure to the organ includes applying a first vacuum pressure to the organ and then applying a second vacuum pressure to the organ, wherein the first vacuum pressure is different than the second vacuum pressure.

14. The method of claim 1, further comprising:
   removing the passive stent from the organ;
   transitioning the organ from the second state to a third state, wherein the organ envelops a third volume in the third state, the third volume being greater than the second volume; and
   affixing a second passive stent to the outer surface of the organ when the organ is in the third state;
   wherein the second passive stent maintains the organ in the third state, and wherein the second passive stent does not further enlarge the organ beyond the third volume.

15. A method for augmenting a patient's organ, comprising:
   affixing a passive stent to an outer surface of the organ after the organ has been transitioned from a first state to a second state, wherein the organ envelops a first volume in the first state and envelopes a second volume in the second state, the second volume being greater than the first volume; and
   maintaining the organ in the second state with the passive stent.

16. The method of claim 15, wherein the organ is an external organ.

17. The method of claim 15, wherein the external organ is a breast.

18. The method of claim 15, wherein the organ is an internal organ.

19. The method of claim 15, wherein affixing the passive stent includes conforming the passive stent to a contour of the organ in the second state.

20. The method of claim 15, wherein affixing the passive stent includes adhering the passive stent to the organ.

21. The method of claim 15, further comprising:
   removing the passive stent from the outer surface of the organ after the organ has been transitioned to the second state;
   affixing a second passive stem to the outer surface of the organ after the organ has been transitioned from the second state to a third state, wherein the organ envelops a third volume in the third state, the third volume being greater than the second volume; and maintaining the organ in the third state with the passive stent, and wherein the second passive stent does not further enlarge the organ beyond the third volume.

* * * * *

UNITED STATES PATENT AND TRADEMARK OFFICE
CERTIFICATE OF CORRECTION

PATENT NO. : 9,522,058 B2  Page 1 of 1
APPLICATION NO. : 14/743968
DATED : December 20, 2016
INVENTOR(S) : Roger K. Khouri et al.

It is certified that error appears in the above-identified patent and that said Letters Patent is hereby corrected as shown below:

In the Claims

In Claim 21, Column 16, Line 66, "stem" should read "stent"

Signed and Sealed this
Twenty-eighth Day of February, 2017

Michelle K. Lee
*Director of the United States Patent and Trademark Office*